United States Patent [19]

Gray et al.

[11] Patent Number: 5,357,696
[45] Date of Patent: Oct. 25, 1994

[54] DEVICE FOR MEASURING FORCE APPLIED TO A WEARER'S FOOT

[76] Inventors: Frank B. Gray, 5104 Lyons View Pike, Knoxville, Tenn. 37919; John L. Parris, 314 Kennon Rd., Knoxville, Tenn. 37909

[21] Appl. No.: 134,962

[22] Filed: Oct. 12, 1993

Related U.S. Application Data

[63] Continuation-in-part of Ser. No. 877,230, May 1, 1992, Pat. No. 5,269,081.

[51] Int. Cl.⁵ .................................................. A61B 5/11
[52] U.S. Cl. .................................... 36/136; 36/137; 128/779; 73/172
[58] Field of Search .............. 36/136, 132, 137, 139; 128/779, 25 B; 73/172; 340/573

[56] References Cited

U.S. PATENT DOCUMENTS

| | | |
|---|---|---|
| 1,933,243 | 10/1933 | De Merolis et al. |
| 3,702,999 | 11/1972 | Gradisar ............ 36/139 X |
| 3,731,674 | 5/1973 | Parvin . |
| 3,791,375 | 2/1974 | Pfeiffer . |
| 3,974,491 | 8/1976 | Sipe . |
| 4,426,884 | 1/1984 | Polchaninoff . |
| 4,503,705 | 3/1985 | Polchaninoff . |
| 4,647,918 | 3/1987 | Goforth . |
| 4,745,930 | 5/1988 | Confer . |
| 4,814,661 | 3/1989 | Ratzlaff et al. |
| 4,918,851 | 4/1990 | Peikin . |
| 5,042,504 | 8/1991 | Huberti ............ 128/779 |
| 5,107,854 | 4/1992 | Knotts et al. |
| 5,113,850 | 5/1992 | Larremore et al. |
| 5,253,654 | 10/1993 | Thomas et al. ............ 128/779 |
| 5,269,081 | 12/1993 | Gray ............ 36/136 |

FOREIGN PATENT DOCUMENTS

3743835 4/1987 Fed. Rep. of Germany .
8200119 4/1982 PCT Int'l Appl. .

OTHER PUBLICATIONS novel electronics inc., "miniEMEDsystem", pp. 1-2.

*Primary Examiner*—Paul T. Sewell
*Assistant Examiner*—Ted Kavanaugh
*Attorney, Agent, or Firm*—Pitts & Brittian

[57] ABSTRACT

A device for monitoring force being applied by a wearer thereof to the wearer's foot, as during walking. The device is contained within a shoe-like structure which can be worn by a recuperating injured person or a person recovering from surgery, etc. The device includes a pressure sensitive element that produces an electrical signal that is related to the force, with this signal being used to alert the wearer when a force in excess of a preselected value occurs. Further, this signal can be used as input to data recording and analysis equipment. The signal transmission can be by direct wire connections, or via radio transmission. A vibratory motion is of particular value to alert the wearer of the point where the excess force occurs. The alerting device can be contained within the shoe, or in other apparatus utilized by a patient. Through the use of this device, a recovering patient will know how much weight to place on the leg in order to achieve maximum healing value.

21 Claims, 6 Drawing Sheets

DEVICE FOR MEASURING FORCE APPLIED TO A WEARER'S FOOT

This is a Continuation-in-Part patent application based upon parent application Ser. No. 07/877,230 filed May 1, 1992, now U.S. Pat. No. 5,269,081 issued Dec. 14, 1993.

TECHNICAL FIELD

This device relates generally to force monitoring systems and, in particular, to systems which measure the force applied to a person's leg during standing, walking, and similar activities. This is useful during rehabilitation of a wearer after surgery, etc. A force sensitive device absorbs the force from the foot, which is then compared to a pre-selected amount of force. When the proper amount of force has been applied to the shoe, a signalling device alerts the patient, such that excessive weight will not be applied.

BACKGROUND ART

During rehabilitation patients are often asked by their physicians to apply a specific amount of weight on a body part, for example, during recuperation following a full knee replacement. While total isolation of the leg may be unnecessary, the leg may not be strong enough to support the full body weight of the person. As a result, the doctor will typically instruct the patient to apply 40%, for example, of his full weight upon the leg. This scenario is also common among other medical treatments such as full or partial hip replacements, healing of broken bones, pulled muscles, etc. In some cases, applied pressure is required for proper healing. For example, medical testing has shown that broken bones heal best along stress lines. Thus, the application of pressure to an injured limb often enhances its recovery.

The amount of force applied to the injured limb is significant because too much force can aggravate injuries, but too little force will not promote healing. For example, if a person is recuperating from a pulled muscle, some force is desired, but if the muscle is not fully recovered, too much pressure can cause re-injury of the muscle. Conversely, if a broken bone is to heal properly, force must be applied to the limb. If too little force is applied, fusion of the bone fragments may not occur and proper healing will take longer than necessary. The patient must apply enough force to aid the healing process, while taking precautions to prevent further damage.

The problem arises in that patients can not always accurately determine how much weight they are applying to their leg. Common practice has been to have the patient stand on a scale and place, for example, thirty pounds on the leg to see how it feels. The patient is then asked to reproduce that feeling with every step, a practically impossible task. A system is required that can sense the amount of weight being applied and then inform the patient when the proper level has been reached.

Prior systems have been developed that study pressure exerted by the foot. Most notably, a system called "Emed" was developed by Novel Electronics Inc. of Minneapolis, Minn. This system requires the patient to walk across an electronic pad, which senses the pressure applied at various points and conveys that information to a computer. Emed is usually operated by a medical practitioner in a doctor's office where it provides complex and detailed stress analysis data. Emed can not be operated by the patient and only returns data from a single step. It is not portable and can not be used during daily walking. A system for promoting the healing of the aforementioned injuries should be able to convey, directly to the patient, information regarding the amount of weight being supported by a limb during every step.

Accordingly, it is an object of the present invention to provide a device that will sense the amount of force being applied upon a leg by every step taken.

It is a further object of the invention to provide a device that will convey a signal to the user when the desired amount of force has been applied to the leg.

It is another object of the present invention to provide a device that will produce an output signal whenever a pre-selected force has been applied such that this output signal can be recorded for future analysis thereof.

Another object of the present invention is to provide a device that will transmit signals relating to the force being applied to a foot such that the same can be recorded at a remote location for analyzing the degree of recovery of a patient, for example.

Further, it is an object of the present invention to provide a shoe-like structure in which is mounted a force sensitive element such that an electrical signal is produced that is related to the amount of force being applied thereto.

A further object of the present invention is to convey to the user a plurality of signals, one of which indicates when the amount of the preselected force has been applied, and at least one at a lesser force.

These and other objects of the present invention will become apparent upon the consideration of the following description with reference to the drawings referred to therein.

DISCLOSURE OF THE INVENTION

According to the present invention there is provided a shoe-like enclosure, referred to hereinafter generally as a shoe, with one or more cavities containing a force concentrating structure, a force monitoring device, and a signalling system. The force concentrating system within the shoe comprises a structure whereby forces are directed primarily to a central point even when distributed unevenly within the shoe. The force monitoring device utilizes force sensing resistors, optical fiber cables, Hall effect devices, other "electronic" devices, or any other suitable means. The force monitoring apparatus then compares the applied force with a desired, pre-selected amount of force. The alert system will notify the shoe wearer when the correct amount of force has been applied. This can be a direct "communication" with the wearer, or the notification can be via the broadcast of signals to a receiver. In one embodiment, the shoe can be worn daily as if it were a normal shoe or, other considerations are provided in an embodiment implemented for people with casts (e.g., a sandal-like unit). An alternate embodiment provides an additional signal to the shoe wearer when some force of a smaller amount has been applied, for example just prior to reaching the preselected amount.

BEST MODE FOR CARRYING OUT THE INVENTION

Figure 1:
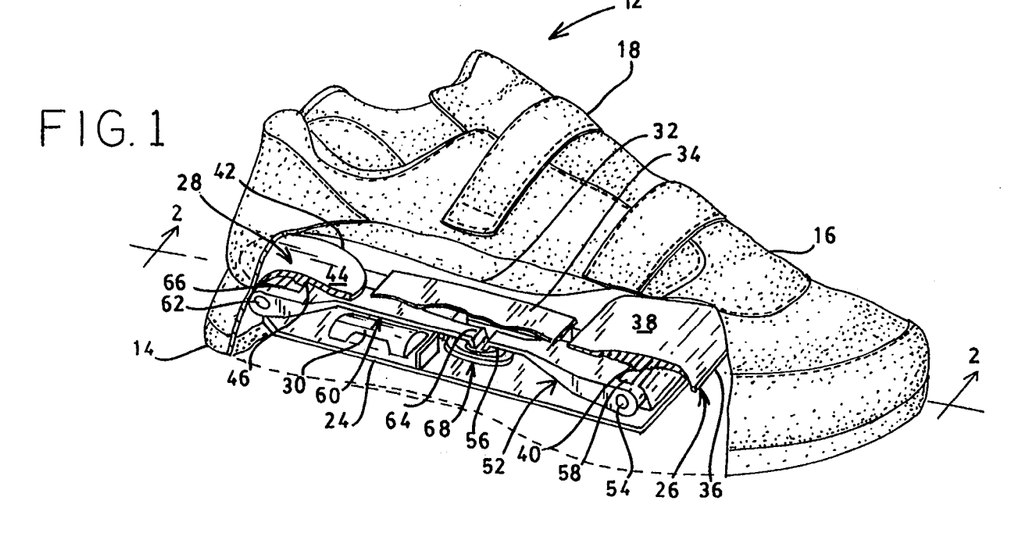
FIG. 1 is a drawing of a preferred embodiment of the present invention, partially cut away, illustrating the relative positions of the components thereof within a shoe.
Figure 2:
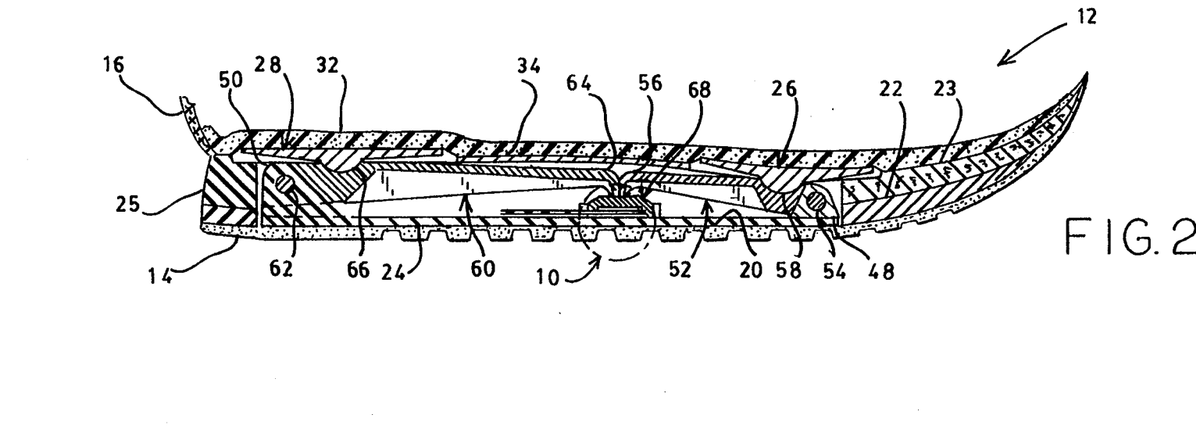
FIG. 2 is a longitudinal cross sectional view of the shoe sole of the shoe of FIG. 1 taken at 2—2 thereof, with the shoe upper removed, illustrating the path of force from the wearer's foot to a force sensing resistor unit of the present invention.

Shown generally at 12 in FIGS. 1 and 2 is a preferred embodiment of the force monitoring shoe of the present invention. The force monitoring shoe 12 is intended to aid in the recovery of patients with insults to the lower extremity and pelvis, such as postoperative states, fractures, and some soft tissue injuries, etc. During the recuperation period, the amount of force applied to the leg is often critical. Inadequate force can hinder the healing process, while undue force can cause additional injuries. This device 12 will monitor the amount of force applied to the leg during every step and give the patient a signal when a pre-selected amount of force has been applied. The amount of force desired is generally the optimal force for promoting healing of the limb at that given point in time, taking into consideration the type of injury and how close to full recovery the patient has come. Further, a signal related to the force can be broadcast by radio transmission to data recording equipment, if desired. This particular embodiment is fabricated to mimic a regular shoe, thus there is a sole portion 14 and an upper 16 to embrace the foot of a wearer (not shown). Preferably the upper takes the form of a walking shoe so as to be quite flexible; however, this is not a requirement of the present invention. Any suitable form of fasteners, such as the hook-and-loop straps 18 can be used to restrain the shoe 12 upon the foot.

In this preferred embodiment, at least one cavity 20 is utilized in the inner surface 22 of the sole 14 to receive a mounting frame 24 to receive the various components of the force monitoring shoe 12, as illustrated in FIGS. 1 and 2. Additional cushioning elements 23 and 25 can be added to minimize the sense of the presence of the frame 24 and its components to adapt an otherwise standard fabricated shoe for the particular application described herein. It will be understood that a combination of cushinging elements 23 and 25 is provided in a shoe construction made specifically for the present invention. The frame 24, for example, supports devices for receiving the force applied by the patient's foot and generating a signal that is compared with a pre-selected desired value. As part of these force receiving devices, there is a first force concentrating unit 26 mounted so as to receive force from proximate the ball of the foot, and a second force concentrating unit 28 mounted proximate the center of the heel- receiving portion of the shoe. Also mounted upon the frame 24 are any electronic components associated with signal conditioning and broadcast (not shown), and a battery 30 for powering the electronics. Some of the electronic components, including a broadcasting antenna, can be located in an additional cavity or cavities (see FIG. 6). All of these components, and others described hereinafter contained within the cavity 20, are covered by a shoe sole liner 32. Further, an "arch support" member 34 gives protection to a central portion of the components such that essentially no force is applied at any points except for the force concentrators 26 and 28.

The two force concentrators 26 and 28 are similar to that disclosed in the aforementioned patent application Ser. No. 07/877,230, with the contents thereof being incorporated herein by reference. For example, force concentrator 26 has a platform 36 to receive pressure from the patient's foot on an upper surface 38, with the lower surface 40 being convex such that pressure applied to the top of the platform is directed to a substantially center location of the lower surface. In a similar manner, the force concentrator 28 has a platform 42 to receive pressure from the patient's foot (the heel) on a top surface 44, with the lower surface 46 being convex such that pressure applied to the top of the platform 42 is directed to a substantially center location of the lower surface. The convex surfaces can approximate either a portion of a sphere or of a right circular cylinder.

The mounting frame 24 has pivot supports 48, 50 at forward and rearward ends. One of these pivot supports (e.g., pivot support can be fabricated as a part of the frame with the other being attached at a position corresponding to a particular shoe size, with extra length of the frame 24 being removed. A first lever member 52 has a first end 54 pivoted from pivot support 48, and a distal end 56 that extends rearward within the frame 24.

This lever member 52 is provided with a concave recess 58 on an upper surface to receive the above-described convex lower surface 40 of the force concentrator 26. A second lever member 60 has a first end 62 pivoted from pivot support 50, and a distal end 64 that extends forward within the frame 24, this distal end terminating proximate the distal end 56 of the lever member 52. The second lever member 60 is provided with a concave recess 66 to receive the convex surface 46 of the force concentrator 28. This recess 66, and recess 58 of lever 52, are preferably semi-cylindrical; however, other shapes are within the scope of the present invention. The convex surfaces 40, 46 of the force concentrators 26, 28 are positioned on each lever at a distance from their individual pivots so as to divide the force whereby the force applied to a signal generating unit (see below) is substantially less than the actual force applied by the patient. Typically a one hundred pound force applied to a platform (36, 42) results in about sixteen and one-half pounds applied to the signal generating element.

Proximate the center of the mounting frame 24 is a signal generating element 68, the output of which is related to the force applied via the distal ends 56 and 64 of the two lever members 52 and 60. This arrangement of levers 52 and 60, together with the signal generating element 68, will be described more fully hereinafter with regard to FIG. 10. Thus, it will be understood that any forces applied to the two force concentrators 26 and 28, as modified by the levers 52, 60, will be generally added and conveyed to the signal generating element 68 by the levers 52 and 60, with the length of the levers and the position of the recesses 58, 66 controlling any desired mechanical advantage. The length of one or more of the levers (e.g., lever 52) is adjusted according to the shoe size, The force division achieved by the lever, however, is not changed.

It will be understood that a single force concentrator having a lever can be utilized with the present invention. For this embodiment, which is not shown, either a heel or a ball position in the shoe can be chosen for the force concentrator.

The signal generating element 68 can take several forms; its function is to provide a signal that is representative of the force being applied thereto. In a preferred form, described in detail with regard to FIG. 7, the signal generating element 68 includes a pressure sensitive resistor pad sandwiched between elements to uniformly distribute the force across the resistor pad. Typically, this resistor pad can be of the force sensing resistor type manufactured by Interlink Electronics of Carpinteria, Calif. When connected to a power source (e.g., the battery 30), any pressure applied to the resistor pad changes the resistance thereof. This resistance change give rise to signals that are related to the pressure (force). The change can be reflected in current change, voltage change, or in the embodiment described hereinafter, as a frequency change. Accordingly, these signals can be used to alert the patient, record the history of forces applied to the limb, etc.

Figure 9:
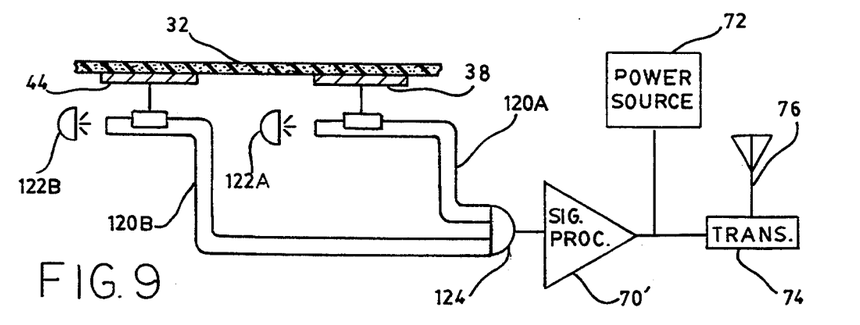
FIG. 9 is a block diagram showing the use of optical fiber cables as a replacement to force resistors in the same manner as in FIG. 8 to convert force to a radio signal and transmit the same, with that signal being converted to a vibrational indication to the wearer of the shoe using a circuit similar to that illustrated in FIG. 3B.

Also, as illustrated in FIG. 9. the pressure sensitive element 68 can be a deformable light pipe, such as an experimental silicone rubber light pipe manufactured by Bridgestone Engineer Products, a Division of Bridgestone Tire and Rubber of Japan. In this embodiment, the applied force reduces the cross-section of the light pipe and thus decreases the light transmission. This change is then used to alert the patient and/or recording of the data.

Other forms of signal generation, based upon a change in force applied by a patient, include hydraulic or pneumatic devices. These take the form of a piston/cylinder or bladder unit, where the pressure is measured with conventional pressure gauges to give rise to the desired signals. Similarly, various solid state devices such as pressure transducers, strain gauges or load cells can be utilized. The output of these also provides a signal for alerting the patient, recording of the data, etc.

Figure 3A:
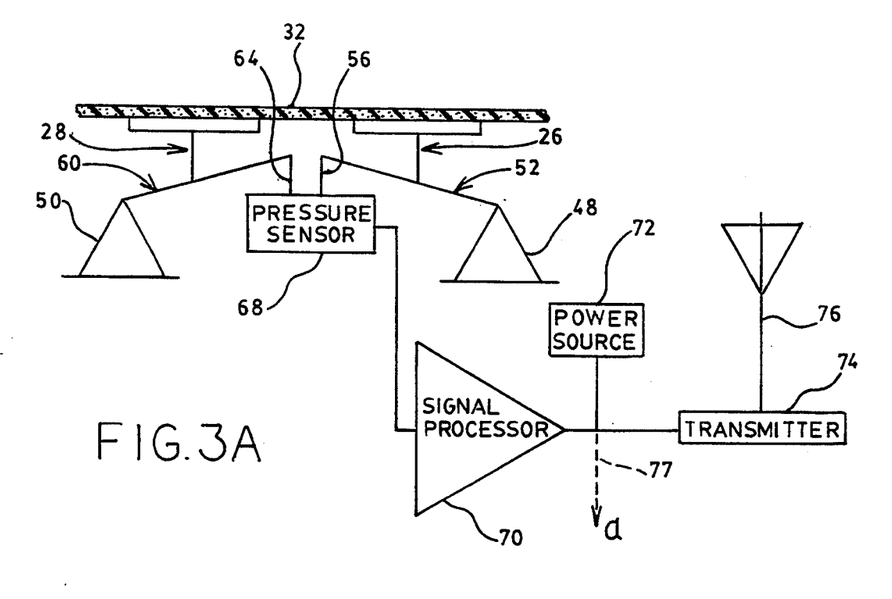
FIGS. 3A and 3B are block diagrams illustrating the electronic components involved in alerting the wearer as to reaching a preselected value of the applied force, including the processing of the signals for radio transmission to a vibration means to alert the wearer of achieving a set force upon the device of FIG. 1.

A block diagram of components (mechanical and electrical) used in association with the embodiment of FIGS. 1 and 2 is shown schematically in FIG. 3A. This depicts the two force concentrators 26 and 28 applying force to the two levers 52, 60, as pivoted from pivot supports 48, 50. The respective distal ends 56, 64 then apply combined forces to the signal generating element 68 of a selected form (see above for discussion of various devices for this function). As will be discussed in greater detail with regard to FIGS. 7 and 10, the signal generating element 68 includes a force measuring element (110 in FIG. 7 and 128 in FIG. 10). An output from the signal generating element 68, typically a value of resistance change as a function of force being applied, is inputted to a signal processing unit 70. In the preferred embodiment, this signal processing unit 70, which includes a timing circuit (see FIG. 11), utilizes the resistance signal to generate an audio tone having a frequency related to that resistance value, with this frequency driving a transmitter (see below). Where there is to be a direct transmission of a signal, this unit 70 can include any comparitor circuits such that the output signal from the signal generating element 68 can be compared with a pre-selected value to set a threshold for further functioning. However, in the preferred embodiment, this signal processing unit 70 is utilized to provide the audio tone frequency signal (via transmission) that alerts the patient of the force (see FIG. 3B). Further, it can be a separate component if desired. Power for the electronics is supplied by the power source 72 (battery 30 or an equivalent). Any desired type of output from the signal processing unit 70 is fed to a broadcast transmitter 74 (typically Model XST-500 E-Z manufactured by XANDI Electronics) and antenna 76.

Figure 3B:
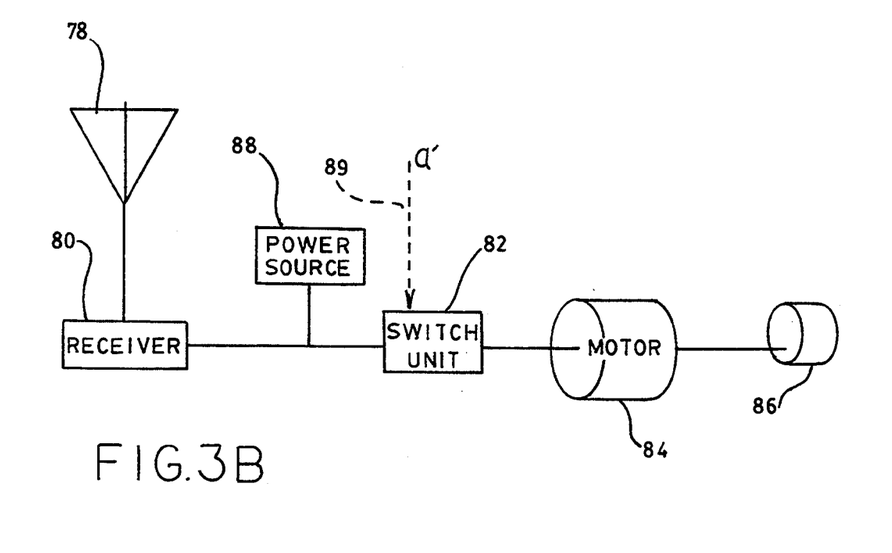
Figure 11:
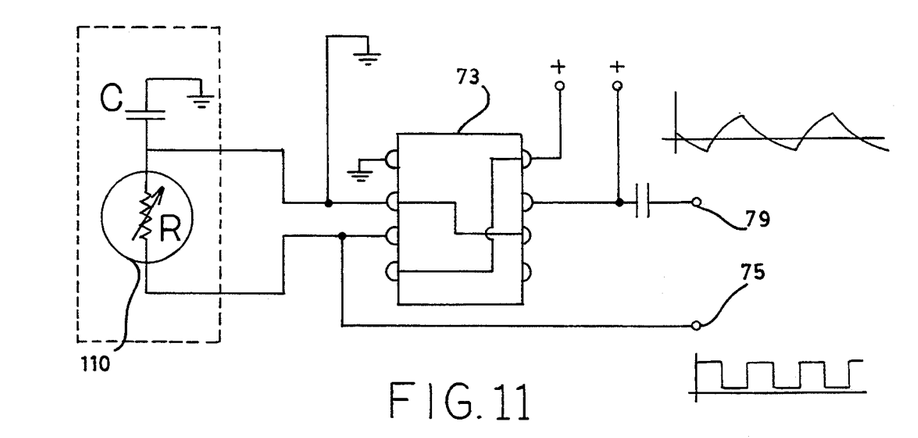
FIG. 11 is a schematic circuit diagram for an audio frequency tone generator useful with the present invention.

A schematic drawing of a specific circuit for generating an audio tone frequency, for the embodiment using a force sensing resistor, is illustrated in FIG. 11. In this circuit, the force sensing resistor (FSR) 110 (FIG. 7) having a variable resistance, R, is coupled with a fixed capacitor, C, such that an output frequency, f, is determined by 1/1.4 RC. The FSR typically has two output connections, with both of these connected to a low power timer 73. This is typically Part No. ICM7555IPA as manufactured by Harris Semiconductor. The result is a pair of signals at outputs 75 and 79. The signal on output 75 is used to control the input into the transmitter 74 (FIG. 3A), while the signal on output 79 is a saw-tooth signal that is used to control the power supply to the transmitter 74 and thus extend the life of the battery As stated above, a radio transmitted signal can be used to alert a patient of a pressure exceeding a pre-selected amount, for example. A circuit for accomplishing this action is illustrated in FIG. 3B. Transmitted signals from the antenna 76 of transmitter 74 (FIG. 3A) are received by antenna 78 for input to a receiver unit 80 (typically a Model TDA-7000 manufactured by Tandy Corporation. This signal is passed through a "switch unit" 82 including a selector switch (typically Model CFG-25 manufactured by Panasonic) for setting a threshold for producing an output, and the resultant signal that is above the threshold powers a motor 84 (typically Model FA-130RA-2270 manufactured by Mabuchi) for driving an eccentric weight 86 or other vibration element such that the patient is made aware of the vibration. Power for this receiving end of the apparatus is provided by a power source 88.

The input signal to the selector switch unit is not completely linear. Accordingly, a portion of the function of the selector switch unit 82 is to adjust for that non-linearity. As will be understood by persons skilled in the art, resistors are inserted between the positions of the selector switch such that each position more correctly responds to a particular force. Thus, one position is typically "OFF" another is 20 pounds force, another is 30 pounds force, etc. Typically, these components used to alert a user will be mounted within an enclosure that can be attached to, or be a part of, a patient-assist structure (walker, etc.), not shown.

Figure 12:
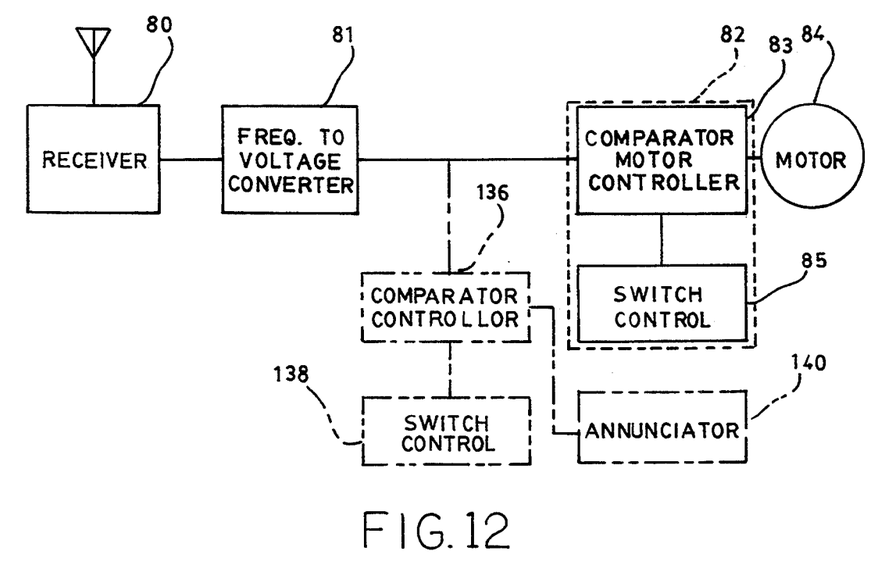
FIG. 12 is a block diagram of two alternate constructions of providing warning signals to a patient.

Shown in FIG. 12 is a block diagram of two alternative embodiments for the portion of the present invention utilized to provide some form of signal to a patient wearing the shoe. The embodiment shown in solid lines throughout is very similar to that described with regard to FIG. 3B. The output of the receiver 80 feeds a frequency-to-voltage convertor 81, with this voltage fed into the switch 82. In actuality, this is a comparator 83 and a switch control 85, the latter being a "dip" switch. When the comparator controller 83 senses a voltage corresponding to a preselected voltage for the frequency related to the force to alert the patient, the afore-mentioned motor 84 is operated.

There may be instances where it will be desirable to alert the patient prior to the set force being reached. Thus, shown in this FIG. 12 with phantom lines is an alternative circuit. For this embodiment, the receiver 80 feeds the convertor el as above. Then, the convertor also feeds a second comparator controller 136 which is controlled by a second switch unit 138. Whenever a signal is received that is equivalent to the set point of the second switch unit, the second comparator controller activates an "annunciator" 140 of any type to alert the patient of this force level. With this circuit alteration, the second comparator 136 and switch 138 can be set to give some sort of output through the annunciator 140 when the frequency detected by the receiver 80 is near, but less, than the frequency at which the first convertor 81 produces an output signal. Of course, it will be understood that other comparator controllers, with appropriate switches, can be used for any preselected level of force.

It will be recognized that if radio transmission is not desired, the vibration mechanism can be positioned within the shoe sole 14 such that the patient can be made aware of the signal alert through his/her foot. Further, wires can directly connect the unit 68 with an alerting device carried elsewhere on the patient. These alternate "direct" connections are indicated by the dashed lines 77 and 89 which would be connected at the points labeled a and a' in FIGS. 3A and 3B, respectively.

It will be recognized that other devices can be utilized to make the patient aware of an arriving signal. There can be sound devices (buzzers or beepers), electric impulses, or some form of light display (LED array). The selection of one or more of the various forms of providing an "alert" signal will depend upon a preferred embodiment; however, the vibrational form illustrated in FIG. 3B overcomes many of the drawbacks of the other enumerated forms and has been found to be compatible with patients.

Figure 4:
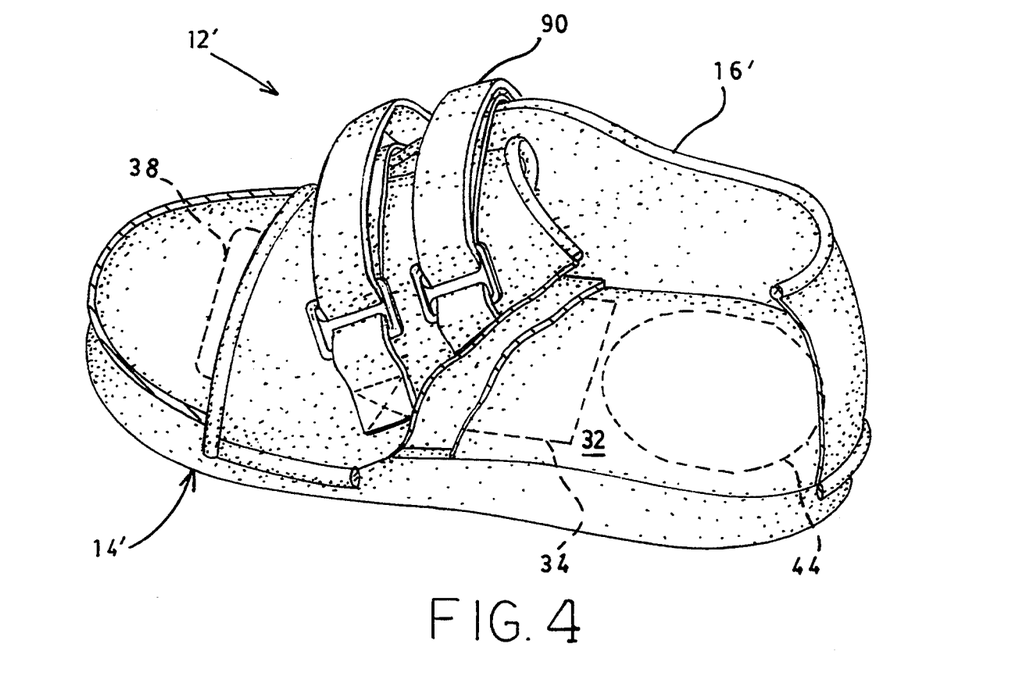
FIG. 4 is a drawing of an alternate embodiment of the present invention, partially cut away, this embodiment of particular use by a patient wearing a foot cast, this embodiment including in a sole portion the components illustrated in FIG. 1 for the preferred embodiment.

Another general embodiment of the present invention is shown at 12' in FIG. 4. Components that are substantially identical with those of FIGS. 1 and 2 carry the same number, while those that are slightly modified but perform the same function carry a primed number. This embodiment is particularly adaptable for persons having a foot cast. Thus, the upper 16' embraces only a portion of the foot cast and is of sufficient size to accommodate such. Various forms of attachment means can be used, such as the hoop-and-loop straps as shown in FIG. 1, or as depicted herein, they can be adjustable straps 90. This embodiment illustrates the platforms 38, 44 in the sole 14' of the same form as in the embodiment of FIG. 1. The electronics and other mechanical components used for this embodiment 12' are like those for the unit of FIG. 1 and FIG. 3A, or can be like those described hereinafter with regard to FIG. 6 and 8.

Figure 5:
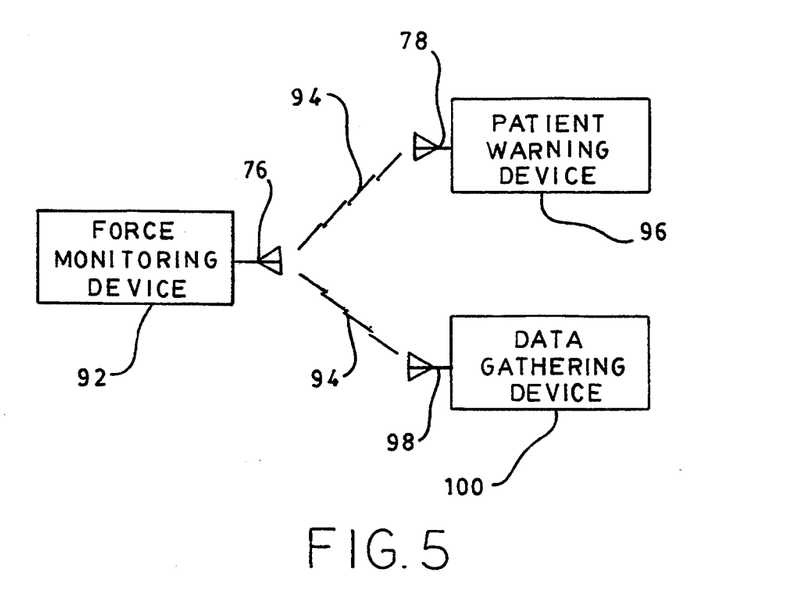
FIG. 5 illustrates, in a block diagram, the transmission of output signals from a force monitoring device to a patient warning device (as in FIG. 3B) and to a data gathering device, such as a recorder.

FIG. 5 illustrates the alternate, or combined, broadcasting of signals from the shoes 12, or 12'. The force monitoring device 92 includes the elements illustrated in FIG. 3A, for example, and broadcasts signals via the antenna 76. These broadcast signals 94 are received by antenna 78 of the patient warning device 96, such as illustrated in FIG. 3B. The same signals 94 can also be received by an antenna 98 of a data gathering device 100, which can be a recorder carried by the patient, a receiver in a physician's office, etc. By the use of electrical signals related to the force, many types of data transmission, analysis and/or storage, can be utilized in the present invention.

Figure 6:
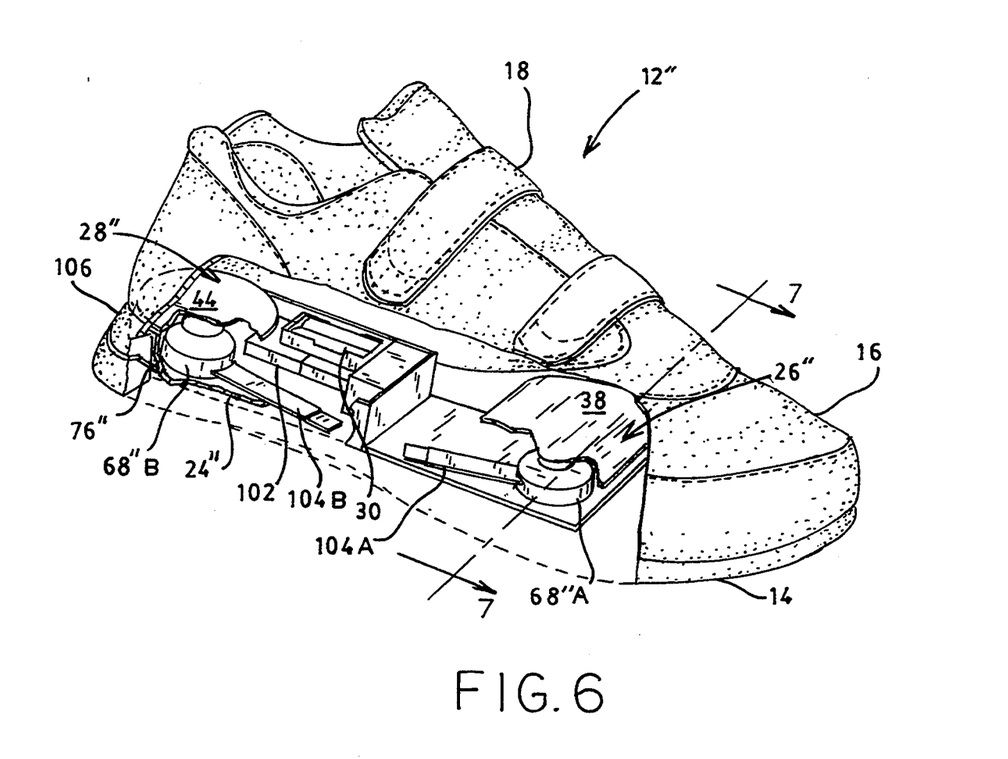
FIG. 6 is a drawing of a further alternate embodiment of the present invention, partially cut away, this embodiment utilizing two force concentrating platforms each with separate force sensing units.

A further embodiment of the present invention is shown at 12'' in FIG. 6. Components that are substantially identical with those of FIGS. 1 and 2 carry the same number, while those that are slightly modified but perform the same function carry a double primed number. Accordingly, this embodiment has a standard sole 14 and upper 16. The attachment means is a set of hook-and-loop straps 18 as in FIG. 1. A mounting frame 24'' is positioned within the upper surface of the sole 14 for the mounting of various components associated with this embodiment. For example, the power source (battery) 30 is mounted therefrom, as are components 102 of the electronics of the system. There are two force concentrators 26'' and 28'' each having platforms 38 and 44, respectively. In contrast to FIGS. 1 and 2, each of the force concentrators has an individual force responsive element as indicated at 68''A and 68''B. Electrical signals from element 68''A are carried to the electronics 102 via leads 104A, while those from element 68''B are carried via leads 104B. As will be discussed in connection with FIG. 8, a portion of the electronics 102 includes a summing circuit as well as an amplifier and transmitter, these components being well known to persons skilled in the art. Indicated in FIG. 6 is a typical location of broadcast antenna 76'' within the periphery of the heel 106.

Figure 7:
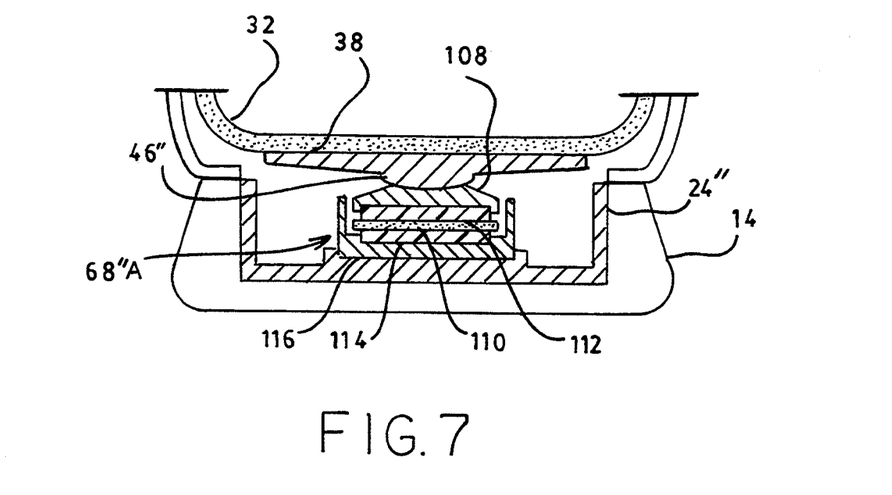
FIG. 7 is a partial cross-sectional view, taken at 7—7 of FIG. 6 illustrating the operation of a force concentrating platform utilized in the present invention.

Typical of the signal generating elements 68'' of FIG. 6 is illustrated in FIG. 7, which is a cross-section taken at 7—7 in FIG. 6. As indicated, the lower surface 46'' of platform 38 is convex, generally as a portion of a cylinder. This convex surface meshes with a anvil 108 having a generally cylindrical recess in the top surface thereof to deliver any applied force to a pressure sensing resistor sheet (or other pressure responsive element) 110, as described above with regard to FIG. 2, so as to generate a signal related to the force. Preferably, the pressure responsive element 110 is sandwiched between resilient members 112, 114 to further uniformly distribute force. These elements are preferably positioned within a cup member 116, which in turn is positioned within the frame 24″. Also, the cup member 116 can be formed as a portion of the frame 24″.

Figure 10:
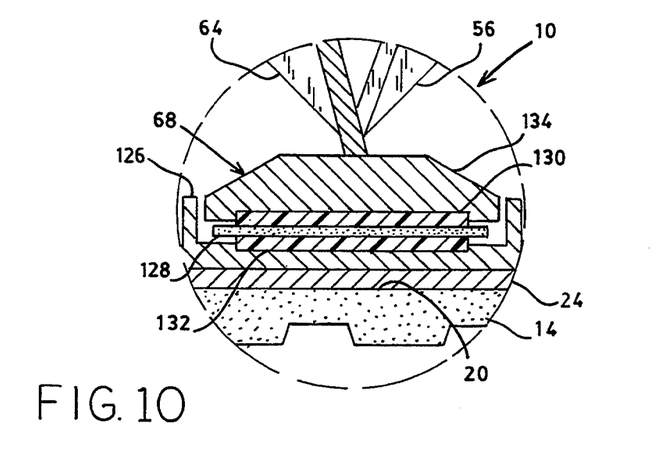
FIG. 10 is a drawing showing an enlarged view of the force sensitive resistor unit utilized in the embodiment of FIGS. 1 and 2 as indicated at the circle 10 in FIG. 2.

The construction of the signal generating element 68″A′ of this FIG. 7 is similar to that of FIGS. 1 and 2, and as further explained in connection with FIG. 10.

Figure 8:
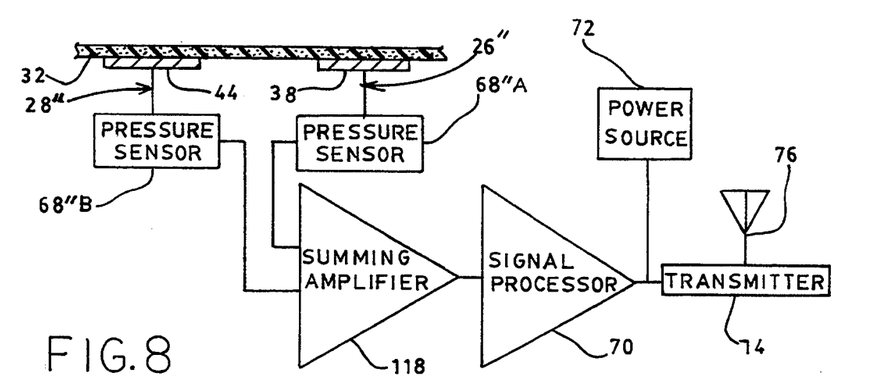
FIG. 8 is a block diagram showing the electronic components involved from the application of force to the force sensing resistors of the embodiment of FIG. 6, to produce a signal to be sent to the wearer via radio transmission, with the signals being received and processed for alerting the wearer with a circuit such as illustrated in FIG. 3B.

Since there is no combining of mechanical forces in this embodiment, in contrast to that of FIGS. 1 and 2, the circuit for achieving a signal for alerting a patient, etc., is illustrated in FIG. 8. Here the signals from the signal generating elements 68″A and 68″B are directed to a summing amplifier 118. The output therefrom is fed to a signal processing unit 70 of the type discussed above in connection with FIG. 3A. The output therefrom goes to a broadcast transmitter 74 and antenna 76. Power is supplied from a power source 72 (e.g., the battery 30). Signals broadcast from the unit can be used with a circuit such as that shown in FIG. 3B to provide a vibratory alert to a patient. Alternatively, the signals can go to a data gathering device as indicated in FIG. 5.

As indicated above, the pressure sensitive element of any of the embodiments can utilize a pressure sensitive light pipe. A schematic circuit of such an embodiment is illustrated in FIG. 9 which is a substantially parallel circuit to that of FIG. 8 in that two sensors are illustrated. The particular light pipe units 120A and 120B are typically a silicone rubber light pipe manufactured by Bridgestone Tire and Rubber Company of Japan. Such light pipes have been shown to have reduced light transmission when pressure is applied transversely. Accordingly, a length of such material 120A is subjected to pressure within the signal generating element. A light source 122, typically in the form of a light emitting diode (LED), sends light along the light pipe to be detected at receiver 124. Similarly, a second length of the silicone rubber light pipe 120B is subjected to pressure at the second signal generating element. A second light source, typically a LED, sends light along this light pipe to also be detected at receiver 124. The sum of the light, in the form of an electrical signal, then is processed in the signal conditioning unit 70′ for driving the radio transmitter 74 and its antenna 76. As in the other embodiments of the circuits, a patient alert mechanism of the type illustrated in FIG. 3B can be used wherein the broadcast signal is received, subjected to threshold detection, and energize a vibration apparatus.

At the heart of the present invention is the force-activated, pressure sensitive detection unit. The details of the preferred embodiment are illustrated in FIG. 10 which is an enlargement of an area of FIG. 2 designated at 10. The mounting frame 24 is provided with a cup 126 similar to the cup 116 of FIG. 7. Alternatively, the mounting frame 24 can be simply provided with a cupped region to provide the same function. Positioned within this cup or cupped region is a "sandwich" assembly of a force sensing resistor 128 similar to that disclosed above interposed between two layers of elastomers 130, 132. An anvil member 134 rests upon the upper of these elastomers, and the distal ends 56, 64 of the two levers 52, 60, respectively, rest upon the upper surface of this anvil member 134. With this construction, forces being transmitted by the two levers 52, 60 are applied at a common area on the anvil member 134 such that a pressure corresponding to the sum of the two forces is applied uniformly to the force sensing resistor 128. Thus, the electrical output from the force sensing resistor is related to the force being applied by a patient to the shoe 12. Having obtained an electrical signal related to the resistance change of this type, the signal processing can proceed as described hereinabove. This permits the switch unit 82 (see FIG. 3B) to receive a non-linear signal derived from the pressure sensitive element and pass a signal to the patient alert circuit when the input signal equals or exceeds that at which the patient is to be alerted. Thus, this switch can be set for any chosen force, such as thirty pounds. When a signal corresponding to that of thirty pounds reaches the switch, the alerting circuits are energized. Of course, should the entire signal be desired for data processing, the entire signal can be sent to that equipment (see FIG. 5). As discussed above, alert signals can be generated at additional levels of applied force if desired.

From the foregoing it will be understood by persons skilled in the art that a foot-wear device has been provided that can be effectively utilized during recovery from various medical conditions that are benefitted from applying a selected force upon the foot. This, then permits an acceptable force to be applied that is beneficial, while warning a patient that excess force is being reached or exceeded such that further damage is prevented. This foot-wear device can be made in the form of a substantially conventional shoe (in outward appearance) or can be fashioned to accommodate a cast or the like. The patient can be alerted to excessive force via radio transmission to some form of "alarm" or direct communication in one embodiment. Further, since the applied force results in an electrical signal related to that force, the signal can be inputted to data processing and storage equipment, either directly or via radio transmission.

Although certain elements are described in great detail, these details are given for a full description and not necessarily for limiting the present invention. Rather, the invention is to be limited only by the appended claims and their equivalents.

We claim:

1. A device for measuring force applied to a foot of a wearer, said device providing an indication to the wearer when the force equals or exceeds a preselected value, said device comprising:

a body member for attachment to a foot of a wearer so as to support at least a portion of the foot, said body member having a sole portion defining an upper surface for support of the foot and a lower surface to contact a support surface, said sole portion provided with at least one cavity, said cavity having a bottom wall;

a covering member to close an upper opening into said cavity;

at least one force concentrator unit within said cavity, said force concentrator unit having a platform with a top surface in contact with said covering member, said platform having a lower surface to concentrate force applied to said platform by the foot to a central location of said force concentrator unit;

a mounting frame within said cavity supported on said bottom wall of said cavity;

a force sensing resistor unit mounted within said cavity and interposed between, and in contact with, said force concentrator unit and a top surface of said mounting frame, said force sensing resistor unit providing a variable electrical output signal whose value is a function of the force applied to said force sensing resistor unit by said force concentrator unit; and a signal processor for receiving said electrical output signal from said force sensing resistor unit.

2. The device of claim 1 wherein said force sensing resistor unit comprises:

an anvil member in contact with said lower surface of said platform;

a force sensing resistor interposed between said anvil member and said top surface of said mounting frame, said force sensing resistor provided with an energizing voltage from a power source, said force sensing resistor having at least one output lead connected to said signal processor; and wherein said output signal from said force sensing resistor unit is related to a varying resistance of said force sensing resistor, which resistance is an inverse function of the force applied.

3. The device of claim 2 wherein said force sensing resistor is sandwiched between a pair of resilient members whereby force applied by said anvil member is distributed uniformly over said force sensing resistor.

4. The device of claim 1 wherein said force concentrator unit has a lever member with a first end attached with a pivot member to said mounting frame, and a distal end in contact with said force sensing resistor unit, said lower surface of said platform contacting said lever member intermediate said first end and said distal end to divide the force applied to said platform as applied to said force sensing resistor unit.

5. The device of claim 1 wherein a pair of force concentrator units are provided within said cavity, a first force concentrator unit positioned proximate a location of a ball of the foot of the wearer and a second force concentrator unit positioned proximate a center of a heel of the foot of the wearer, each said force concentrator units having a platform with a top surface in contact with said covering member, said platform each having a lower surface to concentrate force applied to said platform by the foot to a central location of said force concentrator units; and at least one a pressure sensitive unit mounted within said cavity to receive said concentrated force of at least one of said force concentrator units, said pressure sensitive unit providing an electrical output signal related to force applied to said pressure sensitive unit by said force concentrator units.

6. The device of claim 5 wherein each of said force concentrator units is provided with a force sensing resistor unit to provide individual electrical outputs, and said signal processor combines said output signals from said force sensing resistor units.

7. The device of claim 5 wherein a single force sensing resistor unit is mounted within said cavity; and wherein said first force concentrator unit has a first lever member with a first end attached with a pivot member to said mounting frame, and a distal end in contact with said force sensing resistor unit, said lower surface of said platform of said first force concentrator unit contacting said first lever member intermediate said first end and said distal end to divide the force applied to said platform as applied to said force sensing resistor unit; and wherein said second force concentrator unit has a second lever member with a first end attached with a pivot member to said mounting frame, and a distal end in contact with said force sensing resistor unit, said lower surface of said platform of said second force concentrator unit contacting said second lever member intermediate said first end and said distal end to divide the force applied to said second platform as applied to said force sensing resistor unit.

8. The device of claim 7 wherein said force sensing resistor unit comprises:

an anvil member in contact with said distal ends of said first and second lever members of said force concentrator units; and a force sensing resistor interposed between said anvil member and said top surface of said mounting frame, said force sensing resistor provided with an energizing voltage from a power source, said force sensing resistor having at least one output lead connected to said signal processor, said force sensing resistor sandwiched between a pair of resilient members whereby force applied by said anvil member is distributed uniformly over said force sensing resistor.

9. The device of claim 1 further comprising:

a signal transmitter for receiving an output of said signal processor and for transmitting said output signal;

a signal receiver, having an antenna, for receiving a transmitted signal;

a selector switch unit connected to said signal receiver for setting a signal threshold level for a preselected force to alert the wearer of a force equalling or exceeding said preselected force and for providing an output signal when said signal threshold level is equalled or exceeded; and an alerting device associated with the wearer to provide a sensation to the wearer of the output of said selector switch unit.

10. The device of claim 9 wherein said alerting device is a vibratory unit, said vibratory unit having a motor driven by said signal from said selector switch unit, said motor driving an eccentric weight member to provide vibration for detection by the wearer.

11. The device of claim 1, further comprising:

a selector switch unit connected to receive an output from said signal processor for setting a signal threshold level for a preselected force to alert the wearer of a force equalling or exceeding said preselected force and for providing an output signal when said signal threshold level is equalled or exceeded; and an alerting device associated with the wearer to provide a sensation to the wearer of the output of said selector switch unit.

12. The device of claim 1 further comprising:

a signal transmitter for receiving an output of said signal processor and for transmitting said output signal;

a signal receiver, having an antenna, for receiving a transmitted signal; and data processing equipment attached to said signal receiver for recording said signal received by said signal receiver related to the force applied by the wearer.

13. A device for measuring force applied to a foot of a wearer, said device providing an indication to the wearer when the force equals or exceeds a preselected value, said device comprising:

a body member for attachment to a foot of a wearer so as to support at least a portion of the foot, said body member having a sole portion defining an upper surface for support of the foot and a lower surface to contact a support surface, said sole portion provided with at least one cavity, said cavity having a bottom wall;

means for attaching said body member to the foot of the wearer;

a covering member to close an upper opening into said cavity;

a first force concentrator unit within said cavity, said first force concentrator unit having a platform positioned proximate a location of a ball of the foot of the wearer with a top surface in contact with said covering member, said platform having a lower surface to concentrate force applied to said platform by the ball of the foot to a central location of said first force concentrator unit;

a second force concentrator unit within said cavity, said second force concentrator unit having a platform positioned proximate a center of a location of a heel of the foot of the wearer with a top surface in contact with said covering member, said platform having a lower surface to concentrate force applied to said platform by the heel of the foot to a central location of said second force concentrator unit;

a mounting frame within said cavity supported on said bottom wall of said cavity;

at least one force sensing resistor unit mounted within said cavity and interposed between said first and second force concentrator units and a top surface of said mounting frame, said force sensing resistor unit providing a variable electrical output signal whose value is a function of the force applied to said force sensing resistor unit by said first and second force concentrator units; and a signal processor for receiving said output signal from said at least one force sensing resistor unit.

14. The device of claim 13 wherein each of said force concentrator units is associated with a separate force sensing resistor unit; and wherein said signal processor receives and sums said output signals from both said force sensing resistor units.

15. The device of claim 13 wherein a single force sensing resistor unit is mounted within said cavity; and wherein said first force concentrator unit has a first lever member with a first end attached with a pivot member to said mounting frame, and a distal end in contact with said force sensing resistor unit, said lower surface of said platform of said first force concentrator unit contacting said first lever member intermediate said first end and said distal end to divide the force applied to said platform as applied to said force sensing resistor unit; and wherein said second force concentrator unit has a second lever member with a first end attached with a pivot member to said mounting frame, and a distal end in contact with said force sensing resistor unit, said lower surface of said platform of said second force concentrator unit contacting said second lever member intermediate said first end and said distal end to divide the force applied to said second platform as applied to said force sensing resistor unit.

16. The device of claim 13, further comprising:

a signal transmitter for receiving an output of said signal processor and transmitting said output signal;

a signal receiver, having an antenna, for receiving a transmitted signal;

a selector switch unit attached to said signal receiver for setting a signal threshold level for a preselected force to alert the wearer of a force equalling or exceeding said preselected force and for providing an output signal when said signal threshold level is equalled or exceeded; and an alerting device connected to said selector switch unit, and associated with the wearer, to provide a sensation to the wearer of the output of said selector switch unit.

17. The device of claim 16 wherein said alerting device is a vibratory unit, said vibratory unit having a motor driven by said signal from said selector switch unit, said motor driving an eccentric weight member to provide vibration for detection by the wearer.

18. A device for measuring force applied to a foot of a wearer, said device providing an indication to the wearer when the force equals or exceeds a preselected value, said device comprising:

a body member for attachment to a foot of a wearer so as to support at least a portion of the foot, said body member having a sole portion defining an upper surface for support of the foot and a lower surface to contact a support surface, said upper surface provided with at least one cavity, said cavity having a bottom wall;

means for attaching said body member to the foot of the wearer;

a covering member to close an upper opening into said cavity;

a mounting frame within said cavity supported on said bottom wall of said cavity;

a pressure sensitive unit mounted within said cavity on a top surface of said mounting frame, said pressure sensitive unit providing an electrical output signal related to the force applied to said pressure sensitive unit;

a first force concentrator unit within said cavity, said first force concentrator unit having a) a platform positioned proximate a location of a ball of the foot of the wearer with a top surface in contact with said covering member, said platform having a lower convex surface to concentrate force applied to said platform by the ball of the foot to a central location of said first force concentrator unit, and b) a first lever member having a first end mounted with a pivot to said mounting frame proximate a forward end, and a distal end in contact with said pressure sensitive unit, said lower convex surface of said platform of said first force concentrator in contact with a concave recess in said first lever member intermediate said first end and said distal end;

a second force concentrator unit within said cavity, said second force concentrator unit having a) a second platform positioned proximate a center of a location of a heel of the foot of the wearer with a top surface in contact with said covering member, said second platform having a lower convex surface to concentrate force applied to said second platform the heel of the foot to a central location of said second force concentrator unit, and b) a second lever member having a first end mounted with a pivot to said mounting frame proximate a rearward end, and a distal end in contact with said pressure sensitive unit, said lower convex surface of said second platform in contact with a concave recess on said second lever member intermediate said first and said distal end;

a signal processor for receiving said output signal from said pressure sensitive unit;

a signal transmitter for receiving an output of said signal processor and transmitting said output signal;

a signal receiver, having an antenna, for receiving a transmitted signal;

a selector switch unit connected to said signal receiver for setting a signal threshold level for a preselected force to alert the wearer of a force equalling or exceeding said preselected force and for providing an output signal when said signal threshold level is equalled or exceeded; and an alerting device associated with the wearer to provide a sensation to the wearer of the output of said selector switch unit.

19. A device for measuring force applied to a foot of a wearer, said device providing an indication to the wearer when the force equals or exceeds a preselected value, said device comprising:

a body member for attachment to a foot of a wearer so as to support at least a portion of the foot, said body member having a sole portion defining an upper surface for support of the foot and a lower surface to contact a support surface, said sole portion provided with at least one cavity, said cavity having a bottom wall;

a covering member to close an upper opening into said cavity;

a mounting frame within said cavity supported on said bottom wall of said cavity;

a pressure sensitive unit mounted within said cavity, said pressure sensitive unit providing a variable electrical output signal whose value is a function of force applied thereto;

at least one force concentrator unit within said cavity, said force concentrator unit having a platform with a top surface in contact with said covering member, said platform having a lower surface to concentrate force applied to said platform by the foot to a central location of said force concentrator unit;

a lever member with a first end attached with a pivot member to said mounting frame, and a distal end in contact with said pressure sensitive unit, said lower surface of said platform contacting said lever member intermediate said first end and said distal end to divide the force applied to said platform as applied to said pressure sensitive unit; and a signal processor for receiving said electrical output signal from said pressure sensitive unit.

20. The device of claim 19 wherein said pressure sensitive unit comprises a force sensitive resistor sandwiched between a pair of resilient members and interposed between said top surface of said mounting frame and said distal end of said lever member whereby force applied by said distal end of said lever member is distributed uniformly over said force sensitive resistor, said force sensitive resistor provided with an energizing voltage from a power source, said force sensing resistor having at least one output lead connected to said signal processor.

21. The device of claim 19 wherein said pressure sensitive unit comprises a force sensing light pipe interposed between said top surface of said mounting frame and said distal end of said lever member, said force sensing light pipe provided with an input light at a first end and light receiver at a second end, said force sensing light pipe having a decreased light transmission upon a transverse force being applied to said light pipe by said distal end of said lever member, said light receiver having at least one output lead connected to said signal processor.

* * * * *